(12) United States Patent
Alexandersson (10) Patent No.: US 11,389,590 B2
(45) Date of Patent: Jul. 19, 2022

(54) ADMINISTRATION ASSEMBLY FOR A MEDICAMENT DELIVERY DEVICE

(71) Applicant: SHL Medical AG, Zug (CH)

(72) Inventor: Oscar Alexandersson, Haninge (SE)

(73) Assignee: SHL MEDICAL AG, Zug (CH)

( * ) Notice: Subject to any disclaimer, the term of this patent is extended or adjusted under 35 U.S.C. 154(b) by 157 days.

(21) Appl. No.: 16/500,118

(22) PCT Filed: Mar. 26, 2018

(86) PCT No.: PCT/EP2018/057597
§ 371 (c)(1),
(2) Date: Oct. 2, 2019

(87) PCT Pub. No.: WO2018/192750
PCT Pub. Date: Oct. 25, 2018

(65) Prior Publication Data
US 2021/0106756 A1   Apr. 15, 2021

(30) Foreign Application Priority Data
Apr. 21, 2017 (EP) ..................................... 17167527

(51) Int. Cl.
*A61M 5/20* (2006.01)
*A61M 5/28* (2006.01)
*A61M 5/32* (2006.01)

(52) U.S. Cl.
CPC ............. *A61M 5/20* (2013.01); *A61M 5/285* (2013.01); *A61M 5/3243* (2013.01)

(58) Field of Classification Search
CPC ...... A61M 5/20; A61M 5/285; A61M 5/3243; A61M 2005/2013; A61M 5/2033;
(Continued)

(56) References Cited

U.S. PATENT DOCUMENTS

2008/0015520 A1   1/2008 Hommann et al.
2013/0211342 A1*  8/2013 Raab ................... A61M 5/3158
                                                    604/218
(Continued)

FOREIGN PATENT DOCUMENTS

CA    2445511 A1    11/2002
CN    101087626 A   12/2007
(Continued)

OTHER PUBLICATIONS

Chinese Office Action for CN Application No. 201880024305.2, dated Mar. 2, 2021.

*Primary Examiner* — Brandy S Lee
*Assistant Examiner* — Hong-Van N Trinh
(74) *Attorney, Agent, or Firm* — McDonnell Boehnen Hulbert & Berghoff LLP (57) ABSTRACT

The present disclosure relates to a administration assembly for a medicament delivery device, comprising: an elongated tubular delivery member cover (7), a cartridge holder (11) configured to be received by the delivery member cover (7) and configured to accommodate a medicament cartridge (31), the cartridge holder (11) having a radially flexible and radially inwards extending cartridge blocking protrusion (11b) configured to prevent the medicament cartridge (31) from moving proximally until being subjected to a proximally directed force larger than a threshold value, a needle assembly (13) comprising a double-edged needle having a proximally extending needle portion (13a) and a distally extending needle portion (13b), wherein the needle assembly (13) is configured to be assembled with the cartridge holder (11) so that the distally extending needle portion (13b) extends into the cartridge holder (11), and an administration mechanism including a plunger rod (27) configured to be proximally biased, wherein the delivery member cover (7) is configured to be linearly displaced in the distal (Continued)

direction relative to the cartridge holder (11), and wherein the delivery member cover (7) is configured to activate the administration mechanism when moved in the distal direction, causing the administration mechanism to move the cartridge holder (11) in the proximal direction and to subsequently move the plunger rod (27) in the proximal direction inside the cartridge holder (11) with a force larger than the threshold value.

18 Claims, 6 Drawing Sheets

(58) Field of Classification Search
CPC .... A61M 2005/2073; A61M 2005/208; A61M 5/24; A61M 5/2455; A61M 5/3158; A61M 2005/247; A61M 5/3257; A61M 2005/3258; A61M 5/326; A61M 2005/3261; A61M 2005/3228; A61M 5/3245; A61M 2005/3247; A61M 2005/3254; A61M 2005/3263; A61M 2005/2006; A61M 5/2466; A61M 5/3202
See application file for complete search history.

(56) References Cited

U.S. PATENT DOCUMENTS

| | | | | |
|---|---|---|---|---|
| 2015/0126938 | A1* | 5/2015 | Vogt | A61M 5/326 |
| | | | | 604/192 |
| 2017/0106146 | A1* | 4/2017 | Folk | A61M 5/20 |
| 2017/0136192 | A1* | 5/2017 | Stefansen | A61M 5/2053 |
| 2017/0143903 | A1* | 5/2017 | Helmer | A61M 5/2466 |

FOREIGN PATENT DOCUMENTS

| | | |
|---|---|---|
| CN | 103118723 A | 5/2013 |
| CN | 104379196 A | 2/2015 |
| CN | 106456889 A | 2/2017 |
| EP | 2944341 A1 | 11/2015 |
| JP | 2003-325663 A | 11/2003 |
| WO | 2012022810 A2 | 2/2012 |
| WO | 2014001318 A2 | 1/2014 |
| WO | 2015197867 A1 | 12/2015 |

* cited by examiner

ADMINISTRATION ASSEMBLY FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2018/057597 filed Mar. 26, 2018, which claims priority to European Patent Application No. 17167527.5 filed Apr. 21, 2017. The entire disclosure contents of these applications are hereby incorporated by reference into the present application.

TECHNICAL FIELD

The present disclosure generally relates to medical devices. In particular, it relates to an administration assembly for a medicament delivery device, and to a medicament delivery device comprising an administration assembly.

BACKGROUND

Medicament delivery devices such as auto-injectors may have an auto-penetration mechanism. An auto-penetration mechanism is a spring-tensed arrangement which is shifted proximally. This brings the medicament container and the medicament delivery member forward when the medicament delivery device is activated. To be able to control activation of the medicament delivery device, the medicament delivery member must be prevented from being undesirably pulled forwards.

US 2008/015520 A1 discloses an auto-injector with an active agent container latching. The auto-injector has an elongated casing, in which an active agent container connected to an injection needle can be shifted axially by a spring force. At least one latching tongue prevents the active agent container from being prematurely shifted with respect to the casing, by abutting a flange arranged on a sliding sleeve which accommodates the active agent container. When the auto-injector is placed onto a person's skin, a needle protecting tube is shifted into the casing, forcing the latching tongue away from the flange and, thus, freeing the travel path for needle movement.

According to US 2008/015520 A1 the needle will not be shifted forward to such an extent that it can penetrate the application surface. Moreover, medicament expulsion will not be initiated by this backward-shifting of the needle protecting tube. This requires the user to push the triggering ring at the distal end of the device, which initiates forward movement of the piston rod, and which brings the agent container further forward. Medicament administration hence requires a two-stage user interaction procedure.

SUMMARY

In view of the above, a general object of the present disclosure is to provide an administration assembly for a medicament delivery device which solves or at least mitigates problems of the prior art.

There is hence according to a first aspect of the present disclosure provided an administration assembly for a medicament delivery device, comprising: an elongated tubular delivery member cover, a cartridge holder having a cartridge blocking protrusion configured to prevent the medicament cartridge from moving proximally until being subjected to a proximally directed force, a needle assembly comprising a double-edged needle having a proximally extending needle portion and a distally extending needle portion, wherein the needle assembly is configured to be assembled with the cartridge holder so that the distally extending needle portion extends into the cartridge holder, and an administration mechanism including a plunger rod configured to be proximally biased, wherein the delivery member cover is configured to be linearly displaced in the distal direction relative to the cartridge holder, and wherein the delivery member cover is configured to activate the administration mechanism when moved in the distal direction, causing the administration mechanism to move the cartridge holder in the proximal direction and to subsequently move the plunger rod in the proximal direction inside the cartridge holder with a force larger than a threshold value.

The administration assembly enables auto-penetration and medicament expulsion by a single user interaction by shifting the medicament delivery member cover backwards, i.e. in the distal direction. This movement releases the proximally biased administration mechanism. The proximal movement of the administration mechanism eventually releases the proximally biased plunger rod. The plunger rod will thus move proximally relative to the remaining component(s) of the administration mechanism.

The administration assembly hence provides a two-step proximal movement of the plunger rod. In the first step of the two steps the administration mechanism is activated by the delivery member cover. The activation mechanism, including the plunger rod, is thus moved in the proximal direction. The cartridge holder and the therewith assembled double-edged needle are thus pushed in the proximal direction by the administration mechanism. This proximal movement of the cartridge holder and the double-edged needle provides auto-penetration of the proximally extending needle portion. During this movement of the administration mechanism, the plunger rod is released from its engagement with the remaining component(s) of the administration mechanism. This leads to the second step of proximal movement of the plunger rod, in which the proximally biased plunger rod is moved inside the cartridge holder. The degree of proximal biasing of the plunger rod is such that the plunger rod moves inside the cartridge holder with a force large enough to push a medicament cartridge forward inside the cartridge holder. The force provided by the plunger rod hence disengages the cartridge blocking protrusion from the medicament cartridge. The medicament cartridge will thus be able to move past the cartridge blocking protrusion and be pushed proximally inside the cartridge holder. The distally extending needle portion which is fixedly assembled with the cartridge holder will thus penetrate the proximal end of the medicament cartridge. Medicament administration can thus be provided.

The cartridge holder may be configured to be received by the delivery member cover and configured to accommodate a medicament cartridge.

The cartridge blocking protrusion may be radially flexible and radially inwards extending.

According to one embodiment the cartridge holder tapers in the proximal direction to provide control of proximal movement of the medicament cartridge.

According to one embodiment the cartridge Mocking protrusion is a radially inwards extending arm having an increasing radial thickness in the proximal direction.

According to one embodiment the delivery member cover is designed with a radial clearance relative to the cartridge holder to allow the cartridge Mocking protrusion to flex radially outwards.

According to one embodiment the delivery member cover has an opening configured to align with the cartridge blocking protrusion when the delivery member cover is moved in the distal direction to allow the cartridge blocking protrusion to flex radially outwards.

One embodiment comprises a first flexible needle shield configured to cover the proximally extending needle portion.

According to one embodiment the delivery member cover has a proximal end wall provided with an opening configured to allow the proximally extending needle portion to penetrate it and to prevent the first flexible needle shield from penetrating it.

This ensures that the proximally extending needle portion will not be exposed until the cartridge holder has been moved proximally by the administration mechanism. The sterility of the proximally extending needle portion may thus be ensured.

One embodiment comprises a second flexible needle shield configured to cover the distally extending needle portion.

According to one embodiment the plunger rod has a sharp proximal end portion configured to penetrate a distal fluid barrier of a medicament cartridge.

According to one embodiment the administration mechanism comprises a rotator configured to axially lock the plunger rod, wherein the rotator is configured to move concurrently with the plunger rod when the administration mechanism moves the cartridge holder.

According to one embodiment the administration mechanism comprises an actuator configured to receive the rotator, wherein the actuator is configured to engage with the rotator when the administration mechanism is moved proximally to cause rotation of the rotator and thereby release the plunger rod from the rotator to enable the plunger rod to further penetrate the cartridge holder.

According to one embodiment the delivery member cover is configured to be proximally biased.

There is according to a second aspect of the present disclosure provided a medicament delivery device comprising: a housing, and an administration assembly according to the first aspect, configured to be arranged in the housing.

The medicament delivery device may for example be an injector. The injector may be an auto-injector.

According to one embodiment the delivery member cover is configured to be moved relative to the housing between an extended position relative to the housing and a retracted position relative to the housing, wherein the administration mechanism is configured to be activated by movement of the delivery member cover from the extended position towards the retracted position.

According to one embodiment the delivery member cover is configured to be received by the housing, and wherein the delivery member cover is configured to engage with the housing when the delivery member cover is returned to the extended position from the retracted position.

One embodiment comprises a medicament cartridge configured to be arranged in the medicament container, wherein the medicament cartridge has a proximal fluid barrier configured to be penetrated by the distally extending needle portion and a distal fluid barrier configured to be penetrated by the plunger rod.

There is according to a third aspect of the present disclosure provided a medicament cartridge for a medicament delivery device, wherein the medicament cartridge comprises: a hollow container body having a proximal end provided with a proximal opening and a distal end provided with a distal opening, the proximal opening and the distal opening being axially aligned, an elastic sealing member configured to seal the proximal opening, a proximal fluid barrier provided outside of the sealing member, configured to prevent oxygen from entering the container body through the proximal opening, and a distal liquid barrier configured to seal the distal opening to prevent liquid to escape through the distal opening and to prevent oxygen from entering the container body through the distal opening.

The medicament cartridge is thus fluid-tight and will in particular not allow oxygen to enter the container body containing the medicament. This ensures that the medicament container and in particular the medicament contained therein may be stored for a longer period of time prior to use.

The sealing member is configured to ensure that the medicament cartridge is liquid-tight and has a structure that adapts to the shape of a needle having penetrated the sealing member. The sealing member is hence configured to ensure that liquid contained in the container body may only be expelled through a needle.

The sealing member may for example be a septum.

The proximal fluid barrier may for example be a foil or a film. The proximal fluid barrier may for example be an aluminium foil.

The proximal fluid barrier may comprise a crimp film provided along the periphery of the container body to ensure sealing of the proximal opening.

The distal fluid barrier may for example be a foil or a film. The distal fluid barrier may for example be an aluminium foil.

The distal fluid barrier may comprise a crimp film provided along the periphery of the container body to ensure sealing of the distal opening.

The medicament cartridge may comprise a stopper configured to be arranged inside the container body. The stopper may be configured to be arranged distally inside the container body. The stopper may for example be configured to be located closer to the distal liquid barrier than to the proximal liquid barrier. The stopper may for example bear against the distal liquid barrier.

The medicament cartridge may be configured to be received by the cartridge holder of the administration assembly of the first aspect described herein.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with an administration assembly, refers to that end of the administration assembly which when mounted inside a housing of a medicament delivery device is closest to the proximal end of the medicament delivery device. The proximal end of the medicament delivery device is hence that end which is to be pointed towards the site of injection during medicament expulsion. The same considerations also apply when referring to any component of the administration assembly. The "distal end" is the opposite end relative to the proximal end. With "proximal direction" and, equivalently, "proximally" is meant a direction from the distal end towards the proximal end, along the central axis of the administration assembly. With "distal direction" or "distally" is meant the opposite direction to "proximal direction".

Figure 1A:
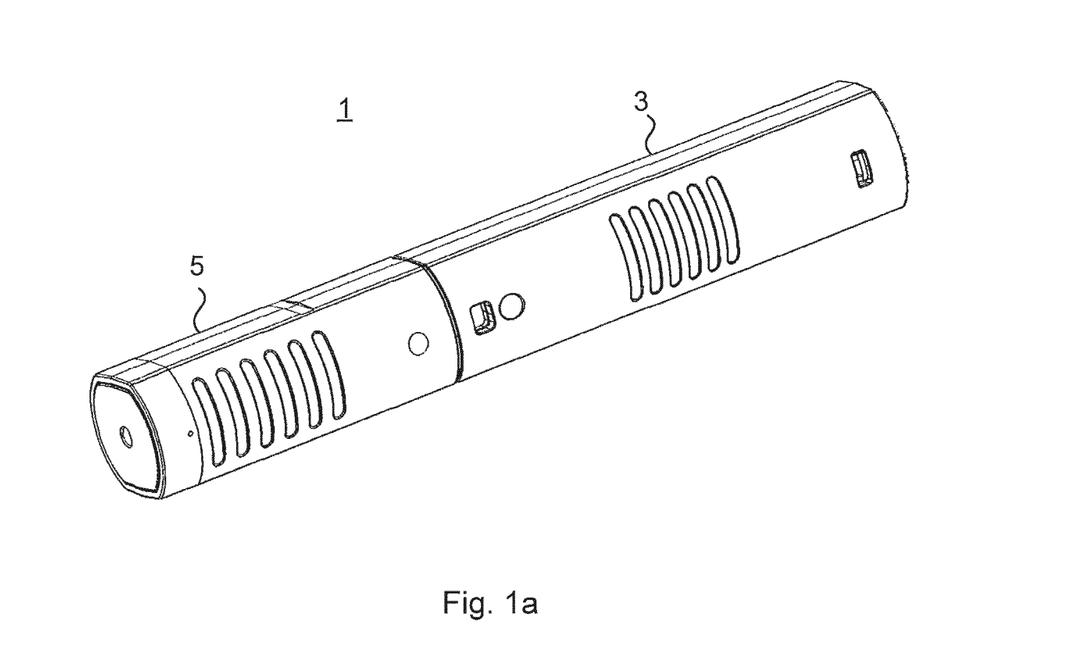
FIGS. 1a and 1b are perspective views of a medicament delivery device.

FIG. 1a shows a perspective view of an example of a medicament delivery device comprising an administration assembly. The medicament delivery device 1 has an elongated housing 3, and a cap 5 configured to protect the delivery member contained inside the housing 3.

Figure 1B:
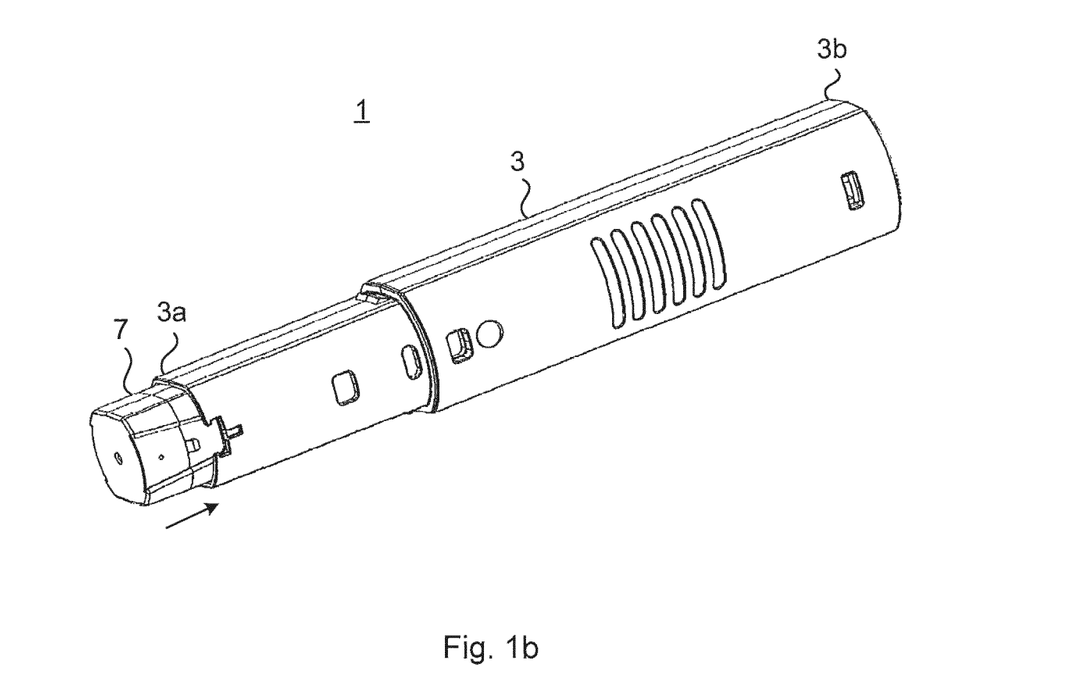

FIG. 1b shows the medicament delivery device 1 with the cap 5 removed. The housing 3 has a proximal end 3a and a distal end 3b. Moreover, the medicament delivery device 1 also has an elongated tubular delivery member cover 7 which is linearly displaceable inside the housing 3, relative to the housing 3. The delivery member cover 7 is biased in the proximal direction. The delivery member cover 7 is movable from an initial extended position relative to the housing 3 shown in FIG. 1b to a retracted position relative to the housing 3. In the extended position a proximal portion of the delivery member cover 7 extends from the proximal end 3a of the housing 3. The direction of movement towards the retracted position is indicated by the arrow. Due to the proximal biasing, the delivery member cover 7 is shifted or displaced proximally when the distally directed force acting on the delivery member cover 7 is removed. The delivery member cover 7 is thus configured to return to the extended position relative to the housing 3 when the distally directed force is removed. According to one variation, the medicament delivery member cover 7 is configured to engage with the housing 3 when returning to the extended position after having been released from the retracted position. The medicament delivery member cover 7 is thus retained in the extended position.

Figure 2A:
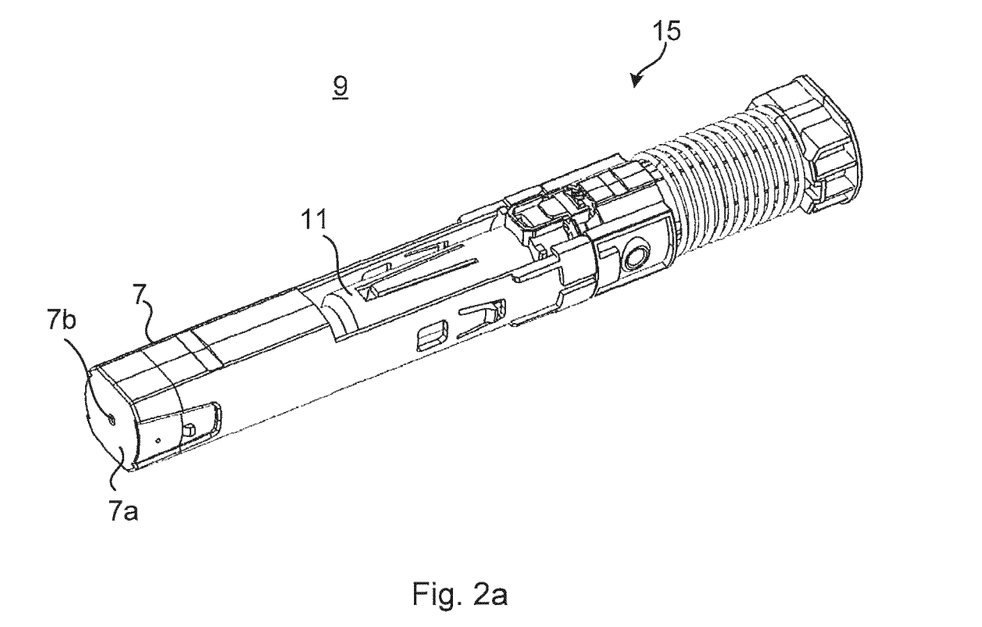
FIGS. 2a and 2b are perspective views of an example of an administration assembly of the medicament delivery device in FIGS. 1a and 1b.

With reference to FIG. 2a, the medicament delivery device 1 also includes an administration assembly 9. In FIG. 2a the housing 3 has been removed to expose an example of an administration assembly 9 in a mounted state. The administration assembly 9 comprises the delivery member cover 7 and a cartridge holder 11 configured to be received by the delivery member cover 7 and configured to accommodate a medicament cartridge. The delivery member cover 7 has a proximal end wall 7a provided with an opening 7b. The administration assembly 9 also comprises a needle assembly 13 illustrated in FIG. 8a, and an administration mechanism 15 configured to be proximally biased.

Figure 2B:
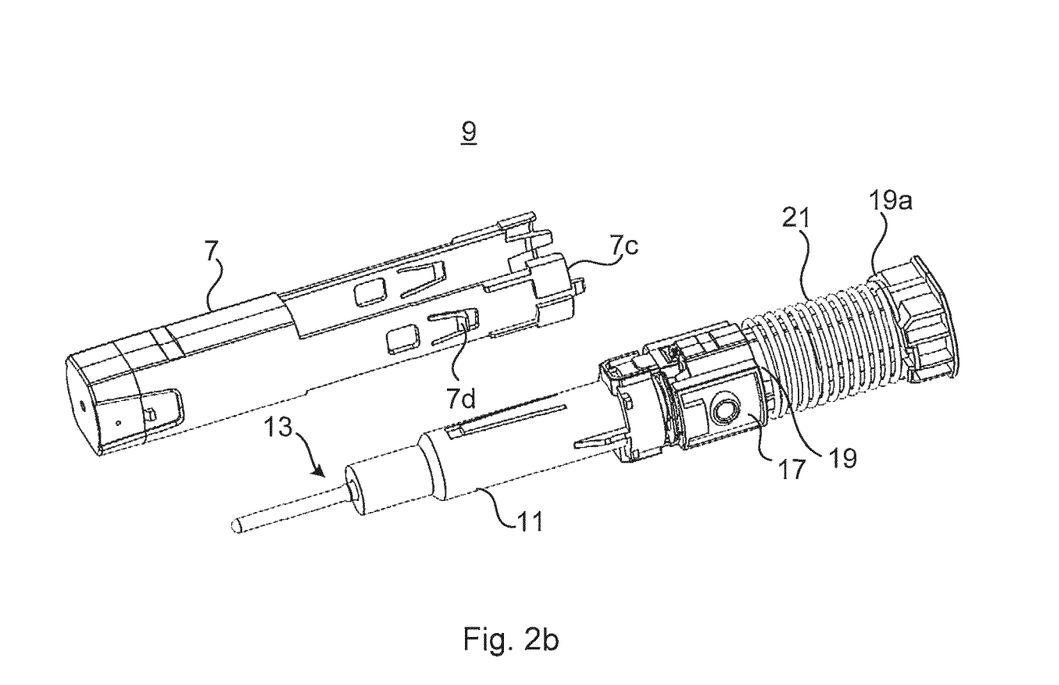

FIG. 2b shows the administration assembly 9 with the delivery member cover 7 removed from the cartridge holder 11. The administration mechanism 15 comprises an actuator sleeve 17, and an actuator 19 received by the actuator sleeve 17. In a mounted state, the distal end 7c of the delivery member cover 7 is arranged proximally with respect to the actuator sleeve 17. The distal end 7c of the delivery member cover 7 may be configured to face the actuator sleeve 17 so that distal movement of the delivery member cover 7 causes the actuator sleeve 17 to move in the distal direction. The delivery member cover 7 is hence configured to actuate the actuator sleeve 17.

The actuator sleeve 17 and the delivery member cover 7 are biased in the proximal direction. The administration mechanism 15 may thus include a first resilient member 21 arranged distally with respect to the actuator sleeve 17. The first resilient member 21 is configured to bias the actuator sleeve 17 proximally. The first resilient member 21 may for example be a spring.

The actuator 19 may according to one variation include a distal flange 19a supporting the first resilient member 21. Distal displacement of the delivery member cover 7 causes the actuator sleeve 17 to move distally. The first resilient member 21 is thereby compressed. The delivery member cover 7 is thus urged by the first resilient member 21 towards its extended position relative to the housing 3.

The delivery member cover 7 is configured to be rotationally locked relative to the housing 3. This can for example be achieved by a structure provided on the outer surface of the medicament delivery member cover 7, configured to engage with a corresponding structure provided on the inner surface of the housing 3. Alternatively, the cross-sectional shape of the delivery member cover 7 and the cross-sectional shape of the inner periphery of the housing 3 may be non-circular.

The actuator sleeve 17 is configured to be rotationally locked relative to the housing 3. The actuator sleeve 17 may for this purpose for example have a guide structure arranged on its outer surface and configured to engage with a corresponding guide structure provided on the inner surface of the housing 3. Alternatively, the cross-sectional shape of the actuator sleeve 17 may have an outer surface which is non-circular and the cross-sectional shape of the inner periphery of the housing 3 may be non-circular.

The delivery member cover 7 may according to one variation include a radial protrusion 7d, or latch, configured to engage with the housing 3 when the delivery member cover 7 returns towards the extended position from the retracted position. The delivery member cover 7 will thereby become axially locked relative to the housing in the extended position. The radial protrusion 7d may extend radially outwards and be radially flexible, allowing it to slide into a recess or opening of the inner surface of the housing 3 to interlock these two components.

Figure 3A:
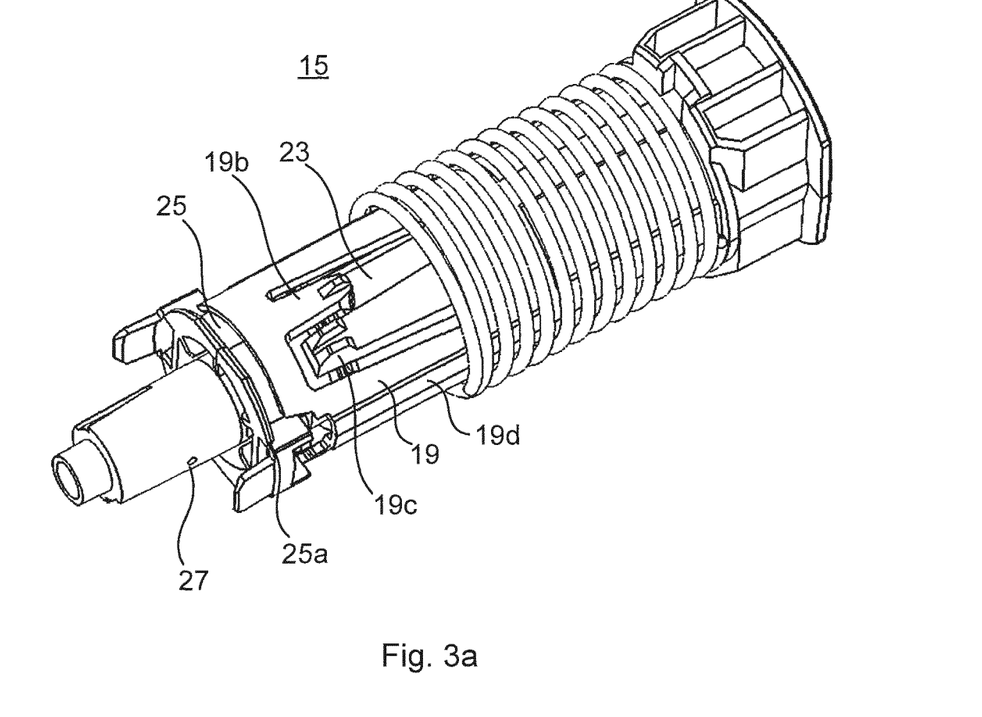
FIG. 3a-c shows an administration mechanism depicted in FIGS. 2a and 2b.

FIG. 3a shows the administration mechanism 15 with the actuator sleeve 17 removed. The administration mechanism 15 further comprises a tubular rotator 23, a plunger holder 25 and an elongated plunger rod 27. The actuator 19 is configured to receive the rotator 23. The rotator 23 is configured to receive the plunger holder 25. The plunger holder 25 is configured to receive the plunger rod 27. The actuator sleeve 17, the actuator 19, the rotator 23, the plunger holder 25 and the plunger rod 27 are arranged concentrically in the listed order, with the actuator sleeve 17 being arranged radially outermost and the plunger rod 27 radially innermost.

The actuator sleeve 17 and the actuator 19 are rotationally locked relative to each other. Since the actuator sleeve 17 is configured to be rotationally locked relative to the housing 3, the actuator 19 is also rotationally locked relative to the housing 3. The actuator sleeve 17 and the actuator 19 are however configured to be axially displaceable relative to each other. The actuator 19 may thus for example comprise one or more axial ribs 19*d* configured to engage with corresponding grooves of the inner surface of the actuator sleeve 17. Relative axial displacement may thereby be provided while preventing relative rotation between these components.

The actuator 19 has a first flexible radially inwards extending portion 19*b*, a latch. The actuator 19 has a second flexible radially inwards extending portion 19*c*. The second flexible radially inwards extending portion 19*c* is prevented from flexing radially outwards by the inner surface of the actuator sleeve 17 when the actuator sleeve 17 is in its initial position. In particular, the inner surface of the actuator sleeve 17 bears against the second flexible radially inwards extending portion 19*c* such that the portion 19*c* bears against a radial surface of the plunger holder 25 in the initial extended position of the delivery member cover 7.

The plunger holder 25 may be provided with a proximal flange 25*a* configured to bear against the medicament container arranged inside the medicament container. Proximal displacement of the plunger holder 25 hence urges the medicament container and the cartridge holder 11 in the proximal direction, providing an auto-penetration functionality. The plunger holder 25 may also be configured to engage with the cartridge holder 11. The plunger holder 25 and the cartridge holder 11 are hence axially interlocked with each other so that axial displacement in the distal direction also results in a corresponding distal displacement of the cartridge holder 11.

Figure 3B:
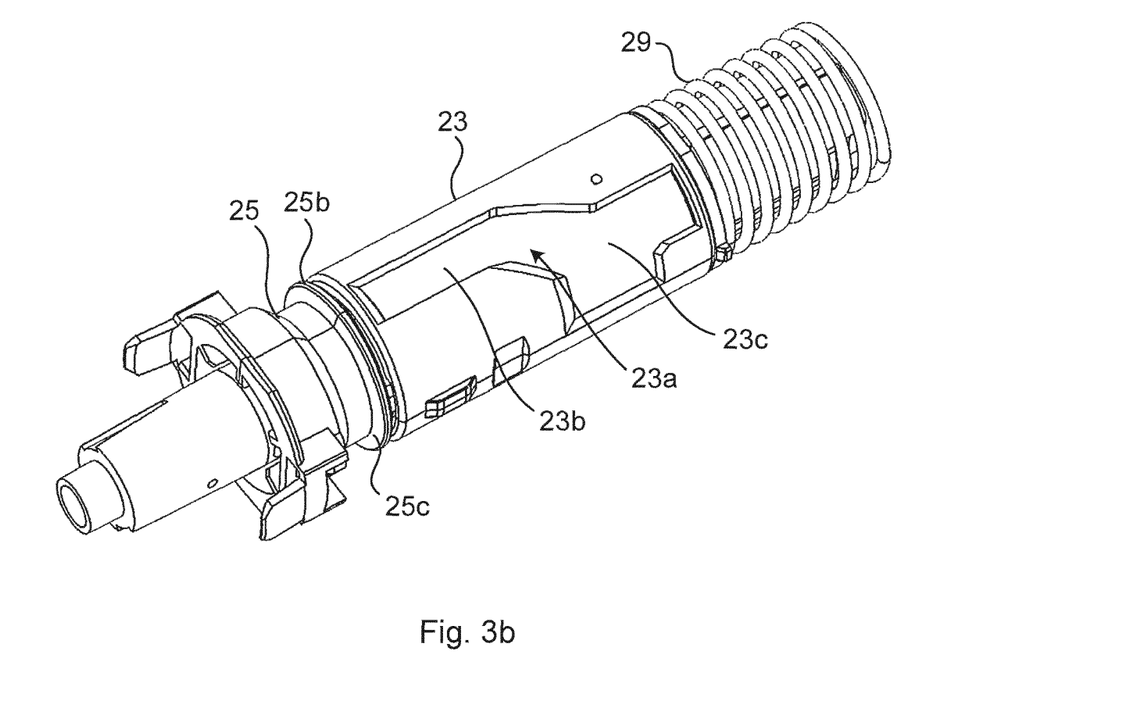

FIG. 3*b* shows the administration mechanism 15 with the actuator 19 removed to expose the rotator 23 which is arranged around the plunger holder 25 and to show a proximal portion of the plunger holder 25. The plunger holder 25 has a radial heel 25*b*, according to the present example a flange, having a radial surface 25*c*. The second flexible radially inwards extending portion 19*c* bears against the radial surface 25*c* in the initial extended position of the delivery member cover 7. The radial surface 25*c* is arranged distally relative to the second flexible radially inwards extending portion 19*c* in the initial extended position of the delivery member cover 7. Moreover, the plunger holder 25 is proximally biased by a second resilient member 29, arranged inside the actuator 19. The radial surface 25*c* prevents the plunger holder 25 from proximal displacement due to the biasing, as long as the second flexible radially inwards extending portion 19*c* bears against the radial surface 25*c*, i.e. as long as the actuator sleeve 17 prevents the second flexible radially inwards extending portion 19*c* from flexing radially outwards.

The rotator 23 bears against a distal surface of the radial heel 25*b*, or flange, which prevents the rotator 23 from independently moving proximally relative to the plunger holder 25. The rotator 23 is also proximally biased. In particular, the rotator 23 is proximally biased by the second resilient member 29.

The rotator 23 has a guide structure 23*a* provided on an outer surface thereof. The guide structure 23*a* includes a proximal portion 23*b* defined by an axial groove portion and a contiguous distal portion 23*c* defined by an inclined groove portion. The inclined groove portion is inclined with respect to a plane extending through the centre of the rotator 23 and parallel with the axial groove portion. The guide structure 23*a*, in particular the axial groove portion and the inclined groove portion are dimensioned to receive the first flexible radially inwards extending portion 19*b* of the actuator 19. The first flexible radially inwards extending portion 19*b* engages with the proximal portion 23*b* of the guide structure 23*a* when the plunger holder 25 has been released by the actuator sleeve 17. As the rotator 23 is moved in the proximal direction by the second resilient member 29, the first flexible radially inwards extending portion 19*b* will slide in the guide structure 23*a* and reach the inclined groove portion, forcing the rotator 23 to rotate.

Figure 3C:
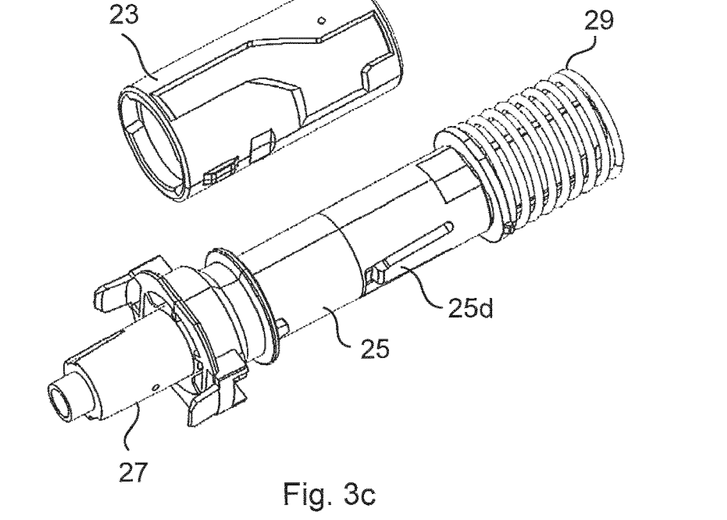

In FIG. 3*c*, the rotator 23 has been moved away from the plunger holder 25 to expose the plunger holder 25. The plunger rod 27 is configured to be proximally biased by a third resilient member, not shown. The third resilient member is arranged inside the hollow plunger rod 27. The plunger holder 25 is configured to initially engage with the plunger rod 27 to prevent the plunger rod 27 from axial displacement in the proximal direction relative to the plunger holder 25. Hereto, according to one variation the plunger holder 25 has one or more flexible radially inwards extending tab(s) 25*d* configured to engage with a corresponding radial opening(s) of the plunger rod 27. The inner surface of the rotator 23 is configured to prevent the flexible radially inwards extending tab 25*d* from flexing radially outwards so that it engages with the radial opening of the plunger rod 27 when the rotator 23 is in its initial position, i.e. prior to rotation. The rotator 23 may for example be provided with a window or opening configured to align with the flexible radially inwards extending tab(s) 25*d* when the rotator is rotated. The flexible radially inwards extending tab(s) 25*d* will thereby be allowed to flex radially outwards as a result of the proximally directed force provided by the third resilient member. The plunger rod 27 is thereby released from its engagement with the plunger holder 25 allowing it to move proximally so that medicament expulsion may be commenced.

Figure 4A:
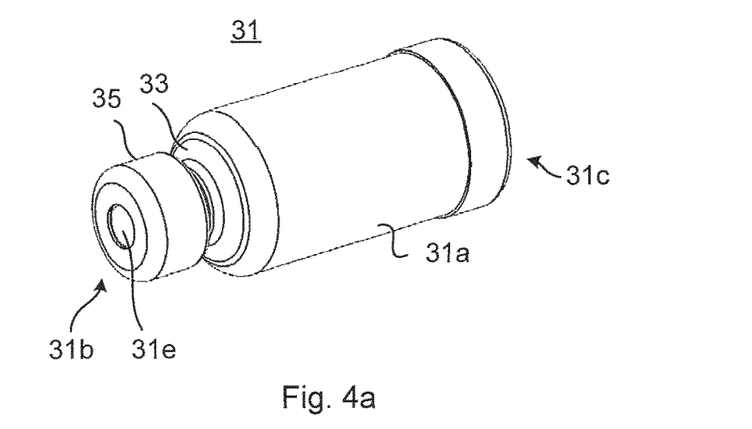
FIGS. 4a and 4b show perspective views of a medicament cartridge.

FIG. 4*a* shows a perspective view of a medicament cartridge 31. The cartridge holder 11 is designed to accommodate the medicament cartridge 31. The medicament cartridge 31 comprises a hollow container body 31*a* configured to accommodate a liquid medicament. The container body 31*a* may for example be composed of glass or a polymeric material. The container body 31*a* may be tapering in the proximal direction. Hereto, the container body 31*a* may have a shoulder portion 33 and a head portion 35 arranged proximally relative to the shoulder portion 33.

The container body 31*a* has a proximal opening 31*b* and a distal opening sic. The proximal opening 31*b* may be provided on the head portion 35 of the medicament cartridge 31. The proximal opening 31*b* and the distal opening 31*c* are axially aligned with each other. The medicament cartridge 31 has an elastic sealing member 31*d*, shown in FIG. 5*a* configured to seal the proximal opening. The elastic sealing member 31*d* is configured to elastically deform around a needle when penetrated to ensure sealing around the needle. The elastic sealing member 31*d* may for example be made of a rubber material.

The medicament cartridge 31 furthermore comprises a proximal fluid barrier 31*e* provided outside of the elastic sealing member 31*d*. The elastic sealing member 31*d* is hence arranged between the space defined by the hollow container body 31a and the proximal fluid barrier 31e. The proximal fluid barrier 31e is arranged proximally relative to the elastic sealing member 31d. The proximal fluid barrier 31e is configured to prevent oxygen from entering the container body 31a through the proximal opening 31b.

Figure 4B:
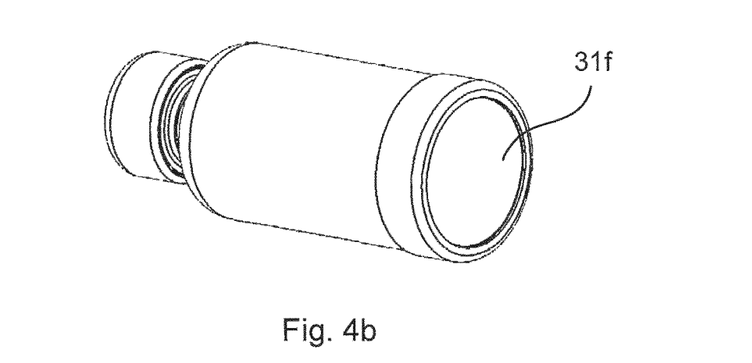

The medicament cartridge 31 comprises a distal fluid barrier 31f, as shown in FIG. 4b. The distal fluid barrier 31f is configured to prevent oxygen from entering the container body 31a through the distal opening 31c and to prevent liquid medicament to escape through the distal opening sic.

The medicament cartridge 31 may furthermore comprise a stopper arranged inside the container body 31a.

Figure 5A:
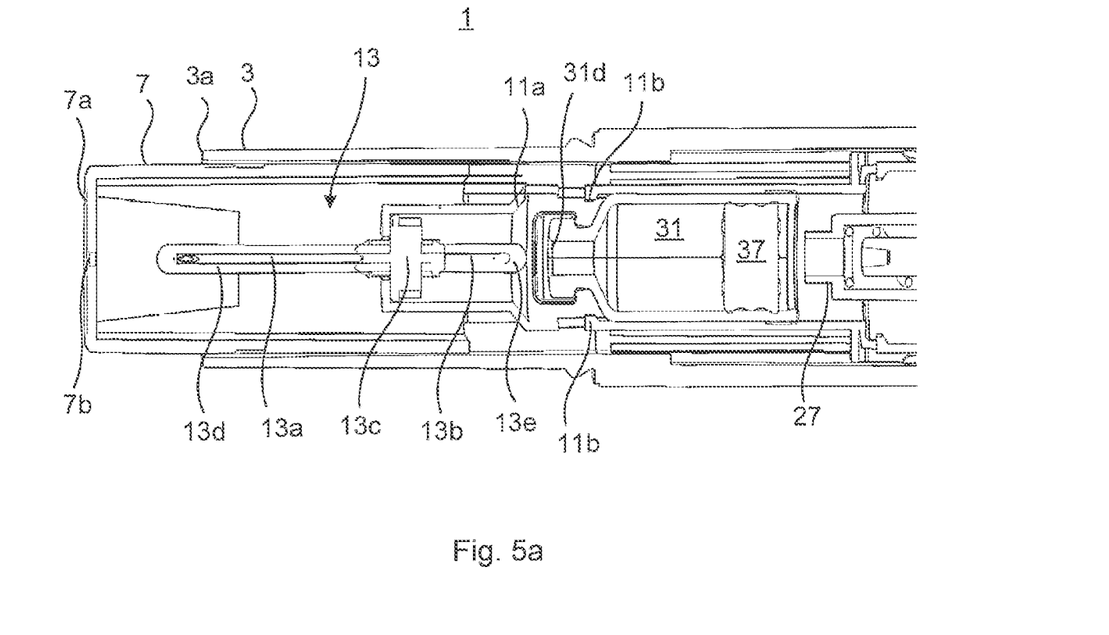
FIGS. 5a-e show longitudinal sections of the medicament delivery device in FIG. 1 in different stages of operation.

FIG. 5a shows a longitudinal section of the medicament delivery device 1 with the cap 5 removed. The medicament delivery device 1 is in its default state, before commencement of medicament administration. The delivery member cover 7 extends proximally through the housing 3 at the proximal end 3a thereof. In FIG. 5a the needle assembly 13 can also be seen. The needle assembly 13 comprises a double-edged needle having a proximally extending needle portion 13a and a distally extending needle portion 13b. The proximally extending needle portion 13a and the distally extending needle portion 13b are coaxial. The needle assembly 13 is configured to be assembled with the cartridge holder 11. The needle assembly 13 has a fixation member 13c through which the needle forming the proximally extending needle portion 13a and the distally extending needle portion 13b extends. The fixation member 13c is configured to be assembled with the cartridge holder 11 to attach the needle assembly 13 to the cartridge holder 11 to prevent the needle assembly 13 from moving axially relative to the cartridge holder 11. The fixation member 13c may be configured to be assembled with a proximal end portion of the cartridge holder 11. The cartridge holder 11 has a proximal opening through which the proximally extending needle portion 13a extends in the proximal direction away from the cartridge holder 11.

The cartridge holder 11 is tapering in the proximal direction. The cartridge holder 11 has a neck portion 11a where the cartridge holder 11 obtains a smaller inner diameter. Proximally from the neck portion 11a there is a proximal end portion of the cartridge holder 11 which has an inner diameter which essentially corresponds to the outer diameter of the head portion 35 of the medicament cartridge 31. The inner diameter of a distal end portion of the cartridge holder, located distally with respect to the neck portion 11a is designed to accommodate the wider container body 31a of the medicament cartridge 31.

The cartridge holder 11 has a radially flexible and radially inwards extending cartridge blocking protrusion 11b. The cartridge blocking protrusion 11b is in the present example a radially inwards extending arm having an increasing radial thickness in the proximal direction. The cartridge blocking protrusion 11b is configured to prevent the medicament cartridge 31 from moving forward inside the cartridge holder 11 until it is being subjected to a proximally directed force larger than a threshold value. When the medicament cartridge 31 is pushed hard enough in the proximal direction, the cartridge blocking protrusion 11b is moved radially outwards, as will be explained in more detail in the following. In order to allow for this radially outwards flexing of the cartridge blocking protrusion 31, the delivery member cover 7, which is moved over the cartridge holder 11, may be sufficiently radially spaced apart from the outer surface of the cartridge holder 11. Alternatively, or additionally, the delivery member cover 7 may be provided with a window, a cut-out, or opening which when aligned axially with the cartridge blocking protrusion 31, allows the cartridge blocking protrusion 31 to flex radially outwards.

In the default state shown in FIG. 5a, the medicament container 31 is arranged distally and spaced apart from the neck portion 11a of the cartridge holder 11. The medicament cartridge 31 also comprises a stopper 37 arranged distally inside the container body 31a. The medicament is located in the volume proximally from the stopper 37.

According to the present example, the needle assembly 13 furthermore comprises sterilisation means. In particular, the needle assembly 13 comprises a first flexible needle shield 13d configured to cover the proximally extending needle portion 13a. The needle assembly 13 comprises a second flexible needle shield 13e configured to cover the distally extending needle portion 13b. The first flexible needle shield 13d is compressible along its longitudinal direction. The second flexible needle shield 13e is compressible along its longitudinal direction.

Figure 5B:
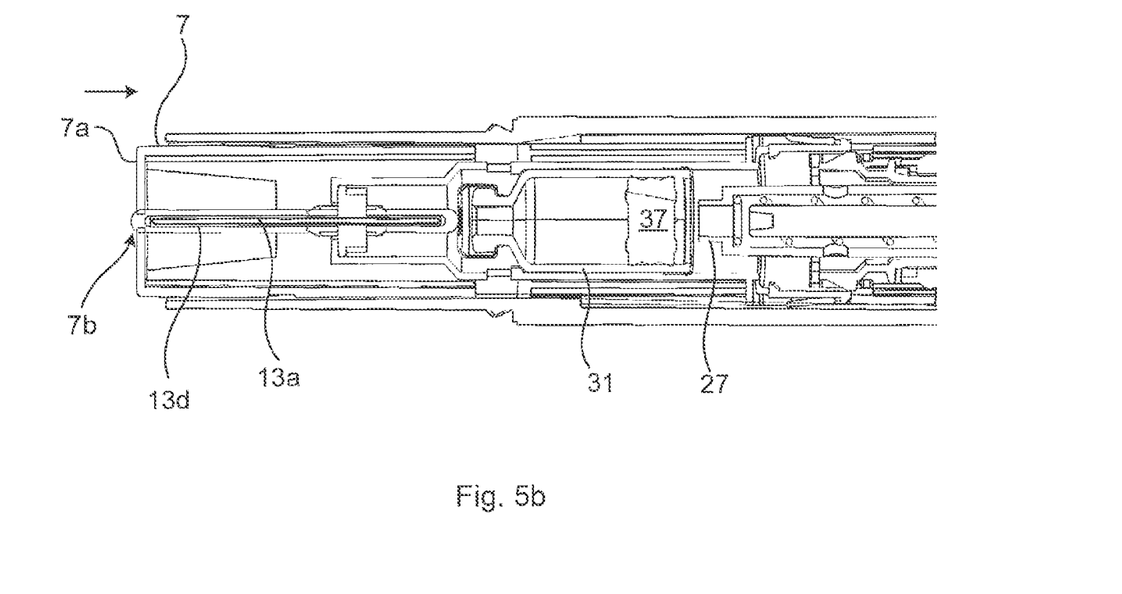

In FIG. 5b, medicament administration has been initiated by movement of the delivery member cover 7 in the distal direction. This is typically obtained by placing the delivery member cover 7 against the injection site and pushing the medicament delivery device 1 towards the injection site. This distal movement of the delivery member cover 7 activates the administration mechanism 15 as has been previously been explained. The first flexible needle shield 13d has impacted the proximal end wall 7a. The opening 7b is too small for the first flexible needle shield 13d to enter but large enough to allow the proximally extending needle portion 13a to pass through. The first flexible needle shield 13d will thus successively be peeled off from the proximally extending needle portion 13a as the delivery member cover 7 is moved proximally. The proximally extending needle portion 13a will on the other hand be able to successively move through the opening 7b as the cartridge holder 11 is moved in the proximal direction.

Figure 5C:
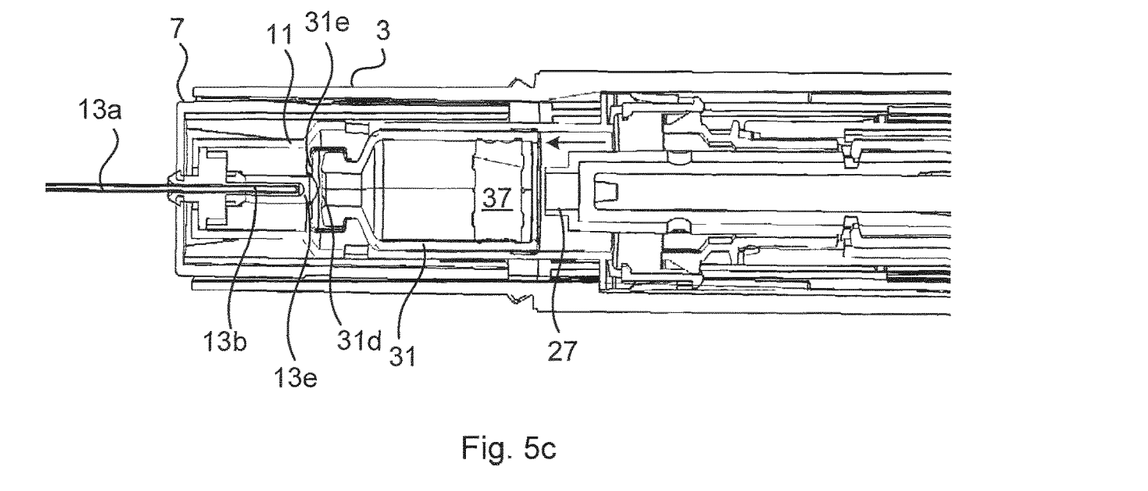

In FIG. 5c the administration mechanism 15 has moved proximally relative to the housing 3 thereby providing the auto-penetration functionality of the medicament delivery device 1. The proximally extending needle portion 13a hence extends from the housing 3. Furthermore, in the figure, the plunger rod 27 has just been released from its engagement with the rest of the administration mechanism 15, in particular from the rotator 23. The plunger rod 27 has thus moved a short distance proximally inside the cartridge holder 11 and pushed the medicament cartridge 31 with a proximally directed force above the required threshold value, causing the cartridge blocking protrusion 11b to release the medicament cartridge 31 so that it can move proximally relative to the cartridge holder 11. The medicament cartridge 31 has also impacted the second flexible needle shield 13d and the distally extending needle portion 13b due to its proximal movement, causing it to penetrate the proximal fluid barrier 31e. With further proximal movement of the medicament cartridge 31, the second flexible needle shield will successively be peeled off from the distally extending needle portion 13b. The distally extending needle portion 13b will eventually penetrate the elastic sealing member 31d and the plunger rod 27 will eventually penetrate the distal fluid barrier 31f.

Figure 5D:
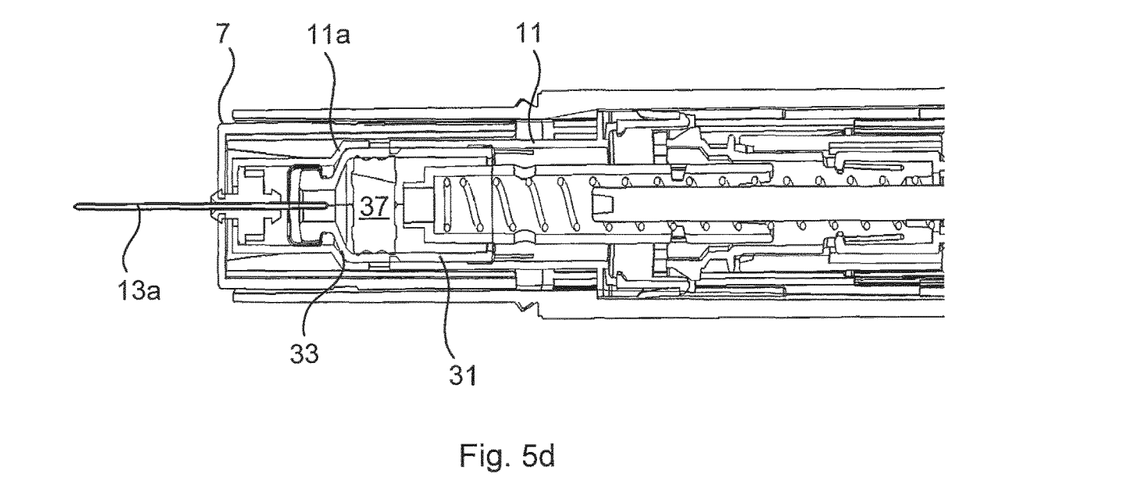

In FIG. 5d, the plunger rod 27 has moved further proximally inside the cartridge holder 11. The medicament cartridge 31 has also moved proximally relative to the cartridge holder 31 with its head portion 35 being guided inside the proximal end portion of the cartridge holder 11. In the state shown in FIG. 5d, the medicament cartridge 31 has reached its final position inside the cartridge holder 11. In this position the shoulder portion 33 of the medicament cartridge 31 abuts the neck portion 11a of the cartridge holder 11.

In the situation shown in FIG. 5d, the plunger rod 27 has penetrated the distal fluid barrier 31f. The plunger rod 27 may for example have a sharp or pointy proximal end to penetrate the distal fluid barrier 31f. The force provided by the biasing of the plunger rod 27 could however be sufficient to penetrate the distal fluid barrier 31f and it may thus not be necessary to provide the plunger rod with a sharp or pointy proximal end. The plunger rod 27 has thus been able to enter the container body 31a through its distal opening sic. Moreover, the plunger rod 27 has pushed the stopper 37 proximally inside the container body 31a whereby medicament has been expelled through the needle formed by the proximally extending needle portion 13a and the distally extending needle portion 13b.

Figure 5E:
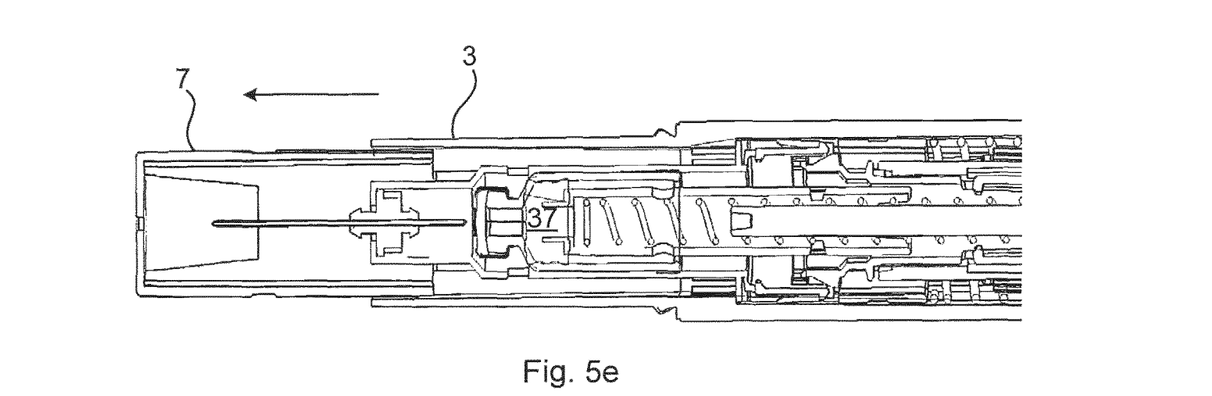

In FIG. 5e the stopper 37 has been fully moved in the proximal direction and the entire dose of medicament contained in the container body 31a has been expelled from the medicament cartridge 31. The medicament delivery device 1 has been removed from the injection site and the delivery member cover 7 has been released from its retracted position and returned to its extended position. In this position, the delivery member cover 7 may engage with the housing 3 so that the delivery member cover 7 remains in the extended position.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. An administration assembly for a medicament delivery device, comprising:
   an elongated tubular delivery member cover,
   a cartridge holder having a cartridge blocking protrusion positioned on a flexible arm and directed radially inward, where the cartridge blocking protrusion prevents a medicament cartridge from moving proximally until being subjected to a proximally directed force which causes the flexible arm to flex radially outward,
   a needle assembly comprising a double-edged needle having a proximally extending needle portion and a distally extending needle portion, wherein the needle assembly is configured to be assembled with the cartridge holder so that the distally extending needle portion extends into the cartridge holder, and
   an administration mechanism including a plunger rod configured to be proximally biased,
   wherein the delivery member cover is configured to be linearly displaced in a distal direction relative to the cartridge holder, and wherein the delivery member cover is configured to activate the administration mechanism when moved in the distal direction, causing the administration mechanism to move the cartridge holder in a proximal direction and to subsequently move the plunger rod in the proximal direction inside the cartridge holder with a force larger than a threshold value.

2. The administration assembly as claimed in claim 1, wherein the cartridge holder tapers in the proximal direction to provide control of a proximal movement of the medicament cartridge.

3. The administration assembly as claimed in claim 1, wherein the flexible arm has an increasing radial thickness in the proximal direction.

4. The administration assembly as claimed in claim 1, wherein the delivery member cover is designed with a lateral space relative to the cartridge holder to allow the cartridge blocking protrusion to flex radially outwards.

5. The administration assembly as claimed in claim 4, wherein the delivery member cover is designed with a radial clearance relative to the cartridge holder to allow the cartridge blocking protrusion to flex radially outwards.

6. The administration assembly as claimed in claim 4, wherein the delivery member cover has an opening configured to align with the cartridge blocking protrusion when the delivery member cover is moved in the distal direction to allow the cartridge blocking protrusion to flex radially outwards.

7. The administration assembly as claimed in claim 1, comprising a first flexible needle shield configured to cover the proximally extending needle portion.

8. The administration assembly as claimed in claim 7, wherein the delivery member cover has a proximal end wall provided with an opening configured to allow the proximally extending needle portion to penetrate it and to prevent the first flexible needle shield form penetrating it.

9. The administration assembly as claimed in claim 1, comprising a second flexible needle shield configured to cover the distally extending needle portion.

10. The administration assembly as claimed in claim 1, wherein the plunger rod has a sharp proximal end portion configured to penetrate a distal fluid barrier to the medicament cartridge.

11. The administration assembly as claimed in claim 1, wherein the administration mechanism comprises a rotator configured to axially lock the plunger rod, wherein the rotator is configured to move concurrently with the plunger rod when the administration mechanism moves the cartridge holder.

12. The administration assembly as claimed in claim 11, wherein the administration mechanism comprises an actuator configured to receive the rotator, wherein the actuator is configured to engage with the rotator when the administration mechanism is moved proximally to cause rotation of the rotator and thereby release the plunger rod from the rotator to enable the plunger rod to further penetrate the cartridge holder.

13. The administration assembly as claimed in claim 1, wherein the delivery member cover is configured to be proximally biased.

14. A medicament delivery device comprising:
   a housing, and
   an administration assembly as claimed in claim 1, configured to be arranged in the housing.

15. The medicament delivery device as claimed in claim 14, wherein the delivery member cover is configured to be moved relative to the housing between an extended position relative to the housing and a retracted position relative to the housing, wherein the administration mechanism is configured to be activated by movement of the delivery member cover from the extended position towards the retracted position.

16. The medicament delivery device as claimed in claim 15, wherein the delivery member cover is configured to be received by the housing, and wherein the delivery member cover is configured to engage with the housing when the delivery member cover is returned to the extended position from the retracted position.

17. The medicament delivery device as claimed in claim 14, comprising a medicament cartridge configured to be arranged in the cartridge holder, wherein the medicament cartridge has a proximal fluid barrier configured to be penetrated by the distally extending needle portion and a distal fluid barrier configured to be penetrated by the plunger rod.

18. An administration assembly for a medicament delivery device, comprising:
   an elongated tubular delivery member cover;
   a cartridge holder having a cartridge blocking protrusion that projects radially inward to prevent a medicament cartridge from moving proximally until the cartridge blocking protrusion is subjected to a proximally directed force which causes the cartridge blocking protrusion to flex radially outward unblocking proximal movement of the medicament cartridge;
   a needle assembly comprising a double-edged needle having a proximally extending needle portion and a distally extending needle portion, wherein the needle assembly is assembled with the cartridge holder before activation of the medicament delivery device such that the distally extending needle portion does not engage the medicament cartridge; and
   a plunger rod that is proximally biased; and
   a rotator configured to axially lock the plunger rod,
   wherein when the delivery member cover is moved axially in a distal direction relative to the cartridge holder, the rotator moves to release the plunger rod such that the plunger rod moves in a proximal direction inside the cartridge holder to move the medicament cartridge with a force large enough to flex the cartridge blocking protrusion radially outward, and
   wherein movement of the cartridge holder proximally causes the distally extending needle portion to extend into the medicament cartridge.

* * * * *